(12) United States Patent
Elbrecht et al.

(10) Patent No.: US 6,537,270 B1
(45) Date of Patent: Mar. 25, 2003

(54) MEDICAL HAND PIECE FOR A LASER RADIATION SOURCE

(75) Inventors: Jens Elbrecht, Jena (DE); Juergen Kuehnert, Jena (DE); Eckhard Schroeder, Eckental (DE); Gabriele Zimmermann, Jena (DE)

(73) Assignee: Asclepion-Meditec AG, Jena (DE)

( * ) Notice: Subject to any disclaimer, the term of this patent is extended or adjusted under 35 U.S.C. 154(b) by 0 days.

(21) Appl. No.: 09/762,834

(22) PCT Filed: Aug. 11, 1999

(86) PCT No.: PCT/EP99/05889

§ 371 (c)(1), (2), (4) Date: Feb. 12, 2001

(87) PCT Pub. No.: WO00/10049

PCT Pub. Date: Feb. 24, 2000

(30) Foreign Application Priority Data

Aug. 13, 1998 (DE) .......................... 198 36 649

(51) Int. Cl.[7] .............................................. A61B 18/18
(52) U.S. Cl. ........................ 606/17; 606/13; 606/15; 606/16; 128/898; 358/4; 358/33
(58) Field of Search ............... 606/4, 5, 9, 10, 606/13–16, 17, 18; 385/4, 31, 33–35; 128/898

(56) References Cited

U.S. PATENT DOCUMENTS

| | | | |
|---|---|---|---|
| 4,852,567 A | * | 8/1989 | Sinofsky .................. 128/303.1 |
| 4,929,246 A | * | 5/1990 | Sinofsky ........................ 606/8 |
| 5,380,318 A | | 1/1995 | Daikuzono |
| 5,507,741 A | * | 4/1996 | L'Esperance, Jr. .............. 606/5 |
| 5,558,666 A | | 9/1996 | Dewey et al. |
| 5,755,751 A | | 5/1998 | Eckhouse |
| 5,860,967 A | * | 1/1999 | Zalvsilan et al. ............... 606/9 |
| 6,102,905 A | * | 8/2000 | Baxter et al. .................. 606/15 |
| 6,213,998 B1 | * | 4/2001 | Shen et al. .................... 606/1 |
| 6,235,017 B1 | * | 5/2001 | Jegorov et al. ............... 606/16 |

FOREIGN PATENT DOCUMENTS

| | | | |
|---|---|---|---|
| DE | 41 03 615 | 8/1992 | |
| DE | 44 29 193 | 2/1996 | |
| DE | 196 23 749 | 5/1997 | |
| FR | 2738082 A1 | * 8/1995 | ........... H01S/3/093 |
| FR | 2 738 082 | 2/1997 | |
| WO | WO 91/04829 | 4/1991 | |
| WO | WO 95/18984 | 7/1995 | |
| WO | WO 98/52481 | 11/1995 | |

OTHER PUBLICATIONS

Naumann Schröder, "Bauelemente der Optik" Carl–Hanser–Verlag München, Vienna, 6th Edition, p. 584.

* cited by examiner

Primary Examiner—Linda C. M. Dvorak
Assistant Examiner—A. Farah
(74) Attorney, Agent, or Firm—Reed Smith LLP

(57) ABSTRACT

A medical handpiece is disclosed which is connected with a laser radiation source via a beam guidance device and by which a laser beam is directed to a treatment area. The handpiece is freely movable to the laser beam source. At least one optical element with a surface which is structured in the micrometer range and which is accordingly micro-optically active is provided inside the handpiece following an exit face of the beam guidance device.

19 Claims, 3 Drawing Sheets

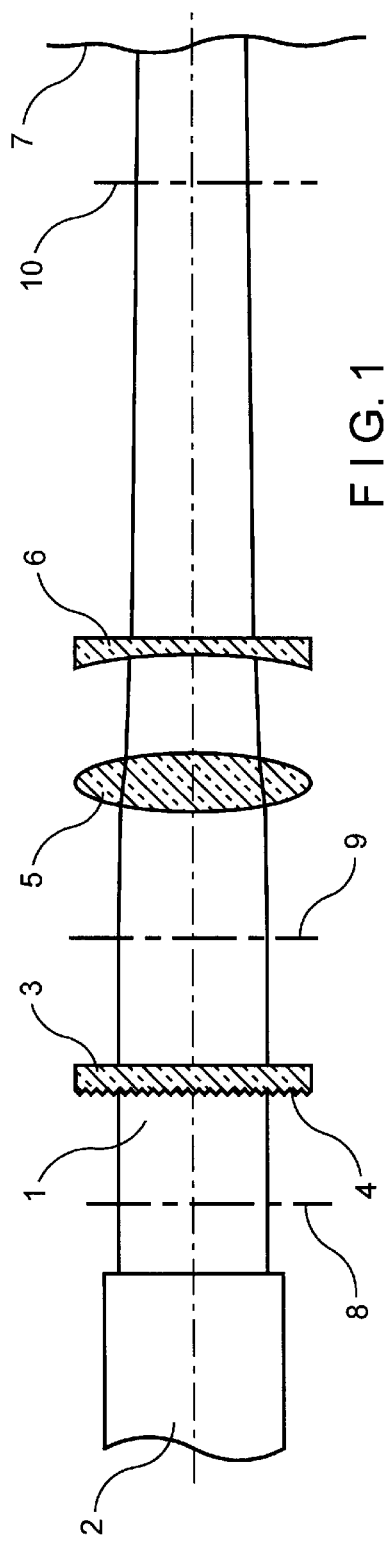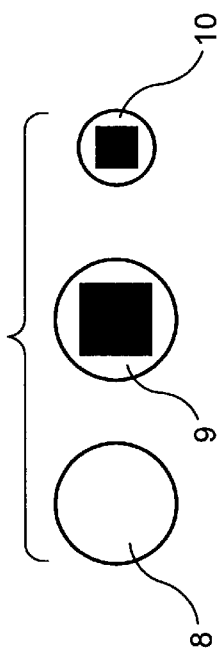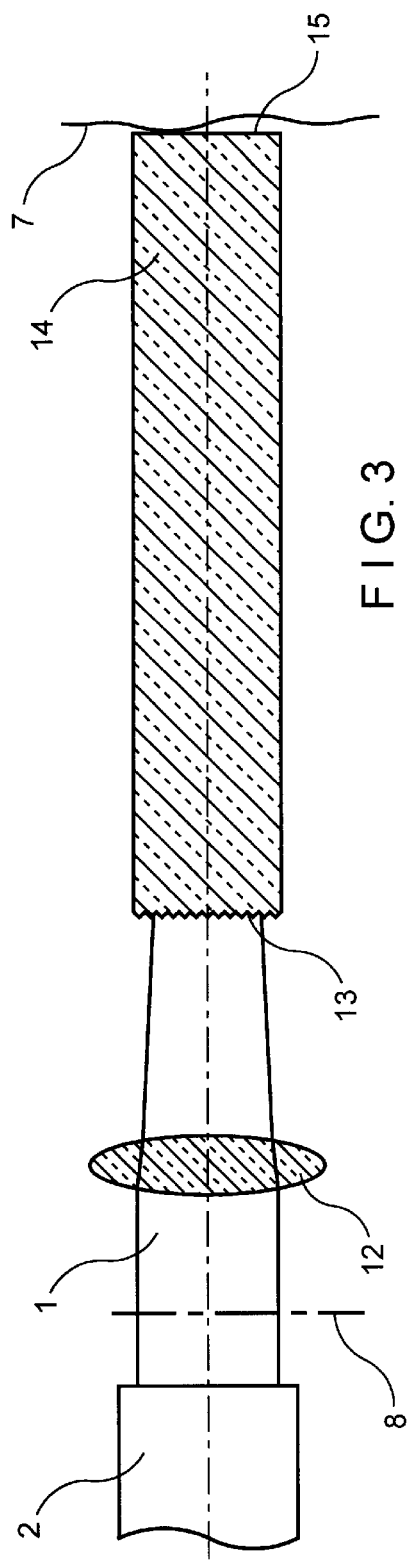

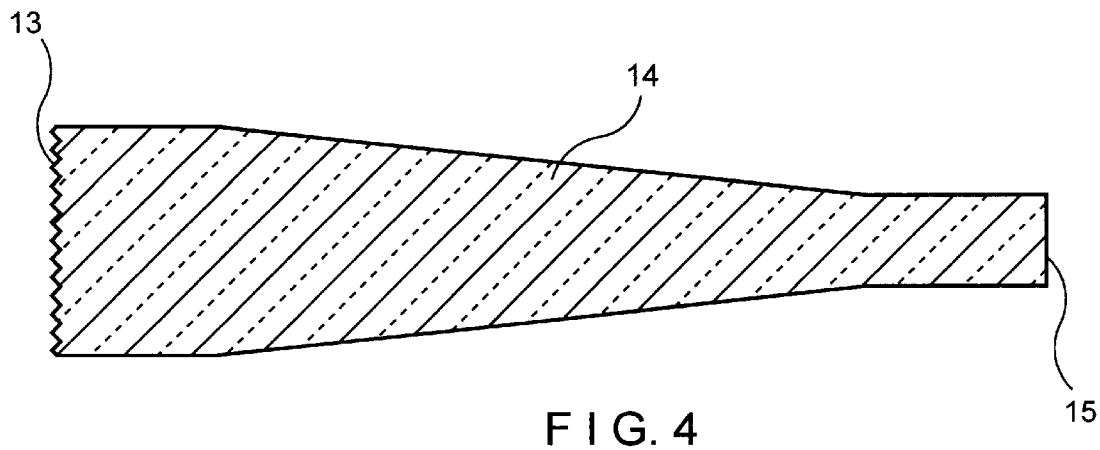
F I G. 4
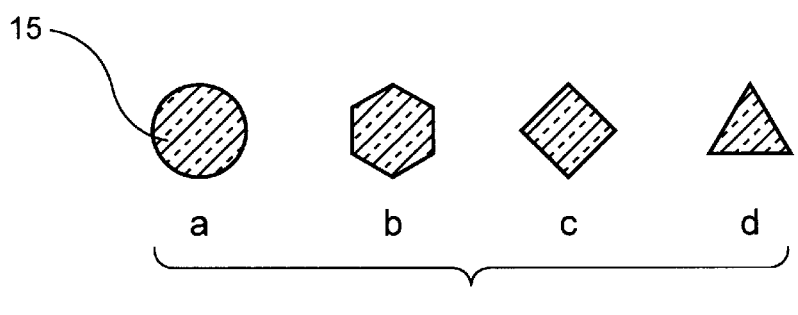
F I G. 5
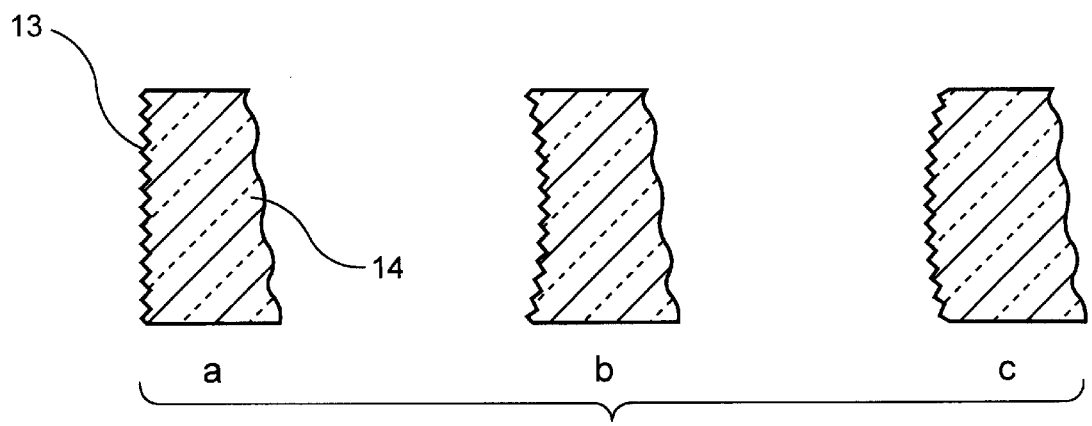
F I G. 6

MEDICAL HAND PIECE FOR A LASER RADIATION SOURCE

BACKGROUND OF THE INVENTION

1. Field of the Invention

The invention is directed to a medical handpiece which is connected with a laser radiation source via a beam guidance device and by which a laser beam is directed to a treatment area, wherein the handpiece is freely moveable relative to the laser beam source. The invention is further directed to a method for cosmetic treatment of skin surfaces using the handpiece according to the invention.

2. Description of the Related Art

In dermatology, laser radiation is frequently used for treatment of port-wine stains, for removal of tattoos, for skin resurfacing and for hair removal. Usually, short laser pulses with a pulse duration in the nanosecond range and microsecond range are introduced into the tissue for this purpose. Treatments of this kind serve primarily to improve the quality of life of the patient and are generally of a cosmetic nature.

The medical technical equipment for carrying out such treatments essentially comprises a laser radiation source and a handpiece which is used for manually directing the beam emitted by the laser radiation source onto the target area.

In order to achieve a lightweight construction of the handpiece and thus to enable the freest possible handling, the laser radiation source and handpiece are constructed as separate subassemblies, wherein the transmission of laser radiation from the radiation source to the handpiece is carried out by means of a movable beam guidance device. The beam guidance device can be formed of a plurality of rigid transmission members interconnected by joints or may also be constructed as a flexible fiber optic system.

The handpieces with which the invention is concerned have an in-coupling element at the transition from the beam guidance device and are outfitted with an emitting surface for the laser beam.

In known handpieces of this type, the emission of the laser beam is carried out with the same characteristics with which it is coupled into the handpiece, i.e., in particular, the distribution of the radiation intensity within the beam cross section and the geometry of the beam cross section are maintained to a great extent and the laser radiation is also directed to the treatment site in this way.

However, for many dermatological applications in which large areas of the skin are to be lased, repeated contiguous placement of the emitting surface is required during treatment in order to cover the entire area to be treated. In so doing, it is important for purposes of uniform treatment of the entire surface that the individual placement surfaces (spots) do not overlap on the one hand, but, on the other hand, also that no areas remain untreated between the placement surfaces.

In this regard, a laser beam with a circular cross section, for example, is disadvantageous because when round spots are placed next to one another there is always overlap or missed locations, so that a uniform radiation of energy into a treatment area is impossible. Accordingly, for effective treatment it is desirable to shape the beam at the emission-side end of the handpiece in such a way that a uniform introduction of energy is ensured when a plurality of spots are rastered on a treatment area.

This is also true for the energy distribution within the laser beam cross section. If the energy density at the edge of the laser beam cross section is less than that in its center, as is the case, for example, with a Gaussian energy distribution, it is not possible to achieve a uniform effect over the entire area of the beam cross section. With laser radiation having a Gaussian energy distribution, it is necessary during treatment to overlap the individual spots in order to achieve approximately continuous treatment results over the entire area to be treated. Of course, this is very difficult to accomplish and depends to a great extent on the sensitivity of the operator and, particularly with uncontrolled overlapping of edge zones, can result in a summing of the energy applied to the parts of the skin at individual locations on the treatment area, causing greater damage to the skin than is desired. Further, the more individual spots must overlap, the longer the duration of the treatment.

The Laid Open Application DE 44 29 193 A1 discloses a device for generating a laser beam with homogeneous cross section which is constructed as a medical handpiece within the meaning of the present new invention. This device can generate radiation which is homogenized with respect to mode and spatially as is required for ablation of the cornea.

A pulsed solid state laser with an emission in the wavelength range of 2 $\mu$m to 3 $\mu$m is used as radiation source. The pulse energy is between 100 $\mu$J and 1 J. A fiber having a length of at least 0.2 m and a diameter between 50 and 1000 $\mu$m is provided for transmitting the energy from the laser arrangement to the handpiece. A transparent rod with circular cross section comprising quartz, sapphire or YAG is provided inside the handpiece following the fiber.

By combining the fiber with the subsequent transparent rod, a beam with a rotationally symmetric intensity profile is achieved at the emission surface; with the latter, the mode mixture emitted by the laser can be effectively converted to the homogenized radially symmetric beam profile, for example, with Gaussian, parabolic or ring-shaped intensity distribution.

However, this handpiece is accordingly not suitable for applications requiring a uniform energy distribution over the entire beam cross section as described above.

OBJECT AND SUMMARY OF THE INVENTION

Based on this prior art, it is the primary object of the invention to further develop a handpiece of the type described above in such a way that a laser beam with a uniform intensity distribution extending to the edge zones of the beam cross section is made available at the emission surface and the geometry of the beam cross section is arranged in such a way that the risk of the target area being affected by unwanted introduction of energy is substantially reduced.

This object is met in a handpiece of the type mentioned above in that at least one optical element with a surface which is structured in the micrometer range and which is accordingly micro-optically active is provided inside the handpiece following the exit face of the beam guidance device.

The optical element with the transparent surface structured in the micrometer range can be realized as a micro-optic array which, by means of diffractive or refractive action, brings about a change in the intensity distribution within the laser beam cross section and/or a beam shaping such that there is a change in cross section.

In a construction of the invention, this surface has a diffractively acting structure whose width is in the order of magnitude of the wavelength of the laser beam utilized for treatment. This can be a height profile varying in this order of magnitude with stripe-shaped, cross-shaped, funnel-shaped and/or otherwise shaped raised portions, an index of refraction varying within the above-mentioned structure width and/or absorption coefficients varying within this structure width. Elements outfitted with surfaces of this type are described, for example, in Naumann, Schröder, "Bauelemente der Optik", Carl Hanser Verlag, Munich, Vienna, 6th edition, page 584.

By means of the surface which is microstructured in this way, the energy distribution within the beam cross section is made uniform to the edge areas when the laser beam passes through this surface, i.e., a radiation intensity which is uniform over the cross section is present in the beam path following this surface over the entire beam cross section.

In a particularly preferred construction, the surface has a refractively acting structure in the form of an array of spherical, aspherical, cylindrical and/or elliptic lenses, wherein each of the lenses has an extension vertical to the beam direction of 10 μm to 1000 μm. These lenses can be arranged hexagonally and/or orthogonally on the surface. They can be concave dispersive lenses or convex collective lenses; concave and convex lenses can also be arranged adjacent to one another on the surface. Randomly oriented concave cutouts are also possible, but notches arranged in a circle or extending helically or intersecting gratings are also suitable.

Preferred dimensions for the refractively acting structures are diameters of 0.35 mm and depths of 0.005 mm. The ratio of depth to diameter should not exceed 0.5. With respect to lens structures, this ratio should be greater than 0.02 and preferably in the range of 0.1 to 0.3.

When the laser beam passes the surface which is structured in this way, the radiation is divided into a plurality of partial beams through the plurality of optically active structure elements (lenses or height profiles), wherein the quantity of partial beams depends on the quantity of structure elements present on the surface. The finer the micro-optically active structure, the more uniform and homogeneous the distribution of the beam intensity over the entire cross section of the laser beam after passing through the described surface. In other words, when passing through the microstructured surface, an uneven energy distribution within the beam cross section is transformed into a uniform energy distribution to the edge areas of the beam cross section.

This homogenization is particularly necessary and advantageous when using a ruby laser as radiation source because, as is well known, its radiation has a highly inhomogeneous intensity distribution in cross section. In addition, the intensity distribution in the ruby laser beam is not constant, but changes from spot to spot, so that when a ruby laser is used without the device proposed according to the invention burning can easily result.

Not only is the intended homogenization of intensity within the beam cross section achieved with the microstructured surface but, depending on the construction of the individual structure elements, the direction of the individual partial beams can also be influenced insofar as this is intended and desired. This means that a laser beam exiting from a fiber, e.g., with circular cross section, can be changed into a laser beam with a square, rectangular, hexagonal or otherwise shaped beam cross section by means of deliberate predetermined shaping of the individual structure elements.

This means that when square, rectangular or hexagonal beam cross sections are directed onto the skin area to be treated, the individual spots can be placed adjacent to one another without overlapping and also without untreated missed locations. Exclusion of overlapping prevents excessive introduction of energy and exclusion of untreated missed locations prevents insufficient introduction of energy, so that the treatment results are significantly improved.

The reshaping of the beam cross section is achieved in that the structure elements on the microstructured surface are selected, shaped and positioned in such a way that the partial beams, especially the peripheral partial beams, are given a direction within the laser beam cross section aiming at a desired outer contour of the cross section. Accordingly, the partial beams no longer fill up a circular beam cross section, but, for example, uniformly fill up a square cross section (the circle segments are cut out).

Accordingly, in relation to the prior art, the handpiece according to the invention is characterized by an intensity of the laser beam at the emission surface that is homogenized over the entire cross section and, moreover, by an adapted cross-sectional shape of the beam.

The micro-optically active structures are easily producible, for example, by means of electron beam lithography, photolithography or ion exchange methods.

In this case, in accordance with the Fresnel equations (relationship between polarization, reflection, absorption), approximately 96% of the laser radiation is coupled in so that the energy loss and accordingly also the heat development is limited to a reasonable amount.

In a development of the invention, a device for beam focusing is arranged in front of and behind the micro-optically structured surface. The size of the beam cross section can be adjusted with this device. For example, a collective lens can be provided as a device of this kind which is positioned in the beam path in front of or after the structured surface.

However, zoom optics can also be provided as a device for beam focusing; with zoom optics it is possible to influence the size of the spot in a simple manner. When the zoom optics are coupled with a corresponding automatic adjustment means, the spot size can be changed during treatment in an uncomplicated manner.

In another construction of the invention, the optical element with the micro-optically active surface is constructed as a beam-guiding rod in which the beam is relayed by total reflection. The rod has an input radiation surface and an emission surface for the laser beam; the input radiation surface is provided with the micro-optically active structure. The beam-guiding rod can be made of silica glass. The size and cross-sectional shape can differ between the input radiation surface and emission surface. Advantageously, however, the input radiation surface should be round, this cross section should be retained over at least 90% of the length of the rod, and a reduction and/or change in the shape of the cross section should be provided only in the remaining length.

Because of the total reflection within the beam-guiding rod, a further "blending" of the plurality of individual partial beams present after passing through the structured surface is achieved and the beam intensity is made more uniform with respect to the beam cross section.

An additional influencing of the beam intensity distributed over the cross section can be achieved when the structured surface is curved, preferably in concave manner, but particularly preferably also in convex manner.

It should be noted that the micro-optic structures, insofar as they are formed on the input radiation surface of a beam-guiding rod as provided according to the invention, can also be the structures of a diffusion plate or scatter disk known from the prior art. However, since the light also enters at an unfavorable angle with the indefinable structures of the scatter disk, the back reflections would result in energy losses and accordingly also in undesirably excessive heat development. But this is prevented by the micro-optically active structures provided according to the invention because they are constructed in such a way that unfavorable entrance angles do not occur.

The emission surface can have a circular as well as a polygonal, e.g., square or hexagonal, cross section.

Further constructions in which a ruby laser or a laser diode integrated in the handpiece are provided as laser radiation source lie within the scope of the invention.

Further, a layer of transparent gel, for example, an ultrasound gel, can be provided between the emission surface and the skin surface to be treated. The radiating of the laser beam into the skin area to be treated is further optimized in this way by reducing the reflection and decreasing scatter. Another result of this is that lower energy densities are needed for the laser light. The refractive index of the gel is to be adapted to the refractive index of the skin and the gel should be transparent at least for the wavelength of the utilized laser light.

In this connection, the object of the invention is met by a method for cosmetic treatment of skin surfaces using the handpiece described above, in which method a gel is applied to the skin area to be treated before the treatment is started, wherein the gel is transparent for the wavelength of the utilized laser light and its index of refraction is adapted to the index of refraction of the skin.

In this way, laser energy is effectively applied to the skin because the light reflected by the skin is reduced to an insubstantial proportion so as to prevent secondary effects which would otherwise occur due to lost heat. An ultrasound gel which is physiologically tolerated and therefore suitable for cosmetic purposes is preferably used. It also has good heat conductivity.

The gel further reduces the risk of damaging the epidermis and prevents formation of smoke and odor during treatment since the skin location to be treated is heated better. The efficacy of the gel can be further increased by removing any hair growth from the part of the skin to be treated before beginning the treatment.

BRIEF DESCRIPTION OF THE DRAWINGS

Shown in the accompanying drawings are:

FIG. 1 a first schematic view of the arrangement according to the invention;

FIG. 2 different beam cross sections;

FIG. 3 a second schematic view of the arrangement according to the invention;

FIG. 4 a construction variant of the rod;

FIG. 5 cross-sectional shapes of the emission surface;

FIG. 6 variants for the design of the input radiation surface;

DESCRIPTION OF THE PREFERRED EMBODIMENTS

Figure 7:
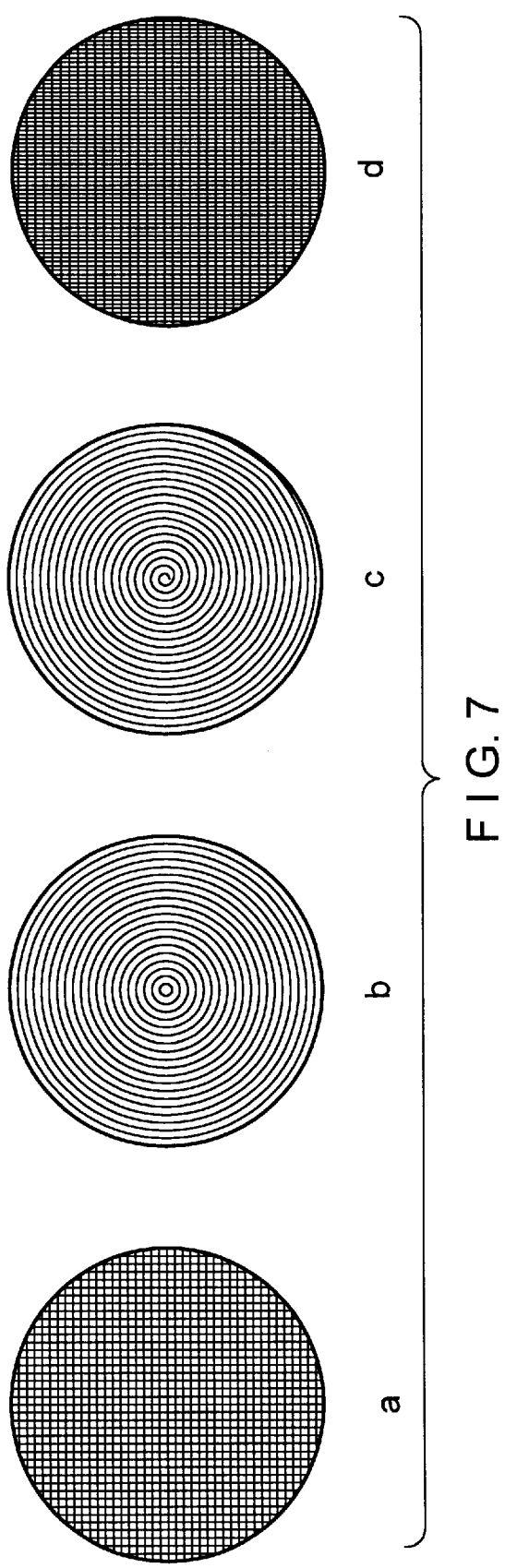
FIG. 7 variants for the design of the microstructure.

FIG. 1 shows the controlling and influencing of the laser beam, according to the invention, within the medical handpiece schematically in a first construction variant. An optical element, for example, a disk 3 made of silica glass and provided with a micro-optically active surface 4, and zoom optics, indicated by lenses 5 and 6, are located in the beam path 1 of a beam guidance device 2 which can be constructed as a flexible light-conducting fiber or in the form of rigid transmission elements which are connected with one another by joints.

With suitable handling of the handpiece, the laser beam is directed onto a part of the skin 7, for example, for purposes of hair removal or for some other cosmetic treatment.

The surface 4 has a refractively active structure, for example, in which a plurality of concave spherical lenses are arranged orthogonal to one another, and is placed in the beam path 1 in such a way that the entire beam path 1 must traverse these microlenses. Each lens has a diameter of approximately 0.35 mm measured at right angles to the beam direction and a depth of 0.005 mm.

A microlens array available, for example, from AMS Mikrooptik GmbH, Saarbrücken, Germany, can be used as disk 3. The differences in position between the individual lenses are less than 0.2 μm. When the laser beam passes through the microlens arrangement on the surface 4, the laser beam is separated into a plurality of partial beams corresponding to the quantity of microlenses.

As a result of this separation into a plurality of partial beams, the circular cross section 8 which is indicated in the beam path 1 and which has a beam with uneven intensity distribution coming from a ruby laser, for example, is transformed into a bean with uniform intensity distribution within a square cross section 9 (see FIG. 2).

With this square cross-sectional shape, the beam is now directed onto the skin part 7 to be treated. The size of the cross-sectional surface 10 impinging on the skin part 7 can be influenced by these zoom optics 5, 6. By varying the zoom optics, the cross-sectional surface 10 can be made larger or smaller, for example. Accordingly, it is possible to adapt to the surface of the area to be treated in an uncomplicated manner.

If the area to be treated is larger than the cross-sectional area 10 that is adjustable by the zoom optics 5, 6, a plurality of spots are placed next to one another on the treatment area 7 in such a way that the treatment area 7 is not only covered without gaps, but the individual spots are also prevented from overlapping.

When the surface 4 is provided with a diffractively active structure instead of with a refractively active structure, the homogenization is not achieved by dividing the laser beam into a plurality of partial beams, but by changing phase. Also, by means of the optical element which is outfitted with this surface, a circular beam cross section with uneven intensity distribution, for example, can be transformed into a square cross section with a uniform intensity distribution. Diffractively active optical elements of this type are produced by and available from BIFO Berliner Institut für Optik GmbH, Rudower Chausee 6, 12484 Berlin, Germany, for example.

FIG. 3 shows a second construction variant of the invention in which the beam path 1 of the laser beam which is coupled in via the beam guidance device 2 initially likewise has a circular cross section 8 with inhomogeneous distribution of radiation intensity. A collective lens 12 is placed in this beam and focuses the laser beam on the input radiation surface 13 of a beam-guiding rod 14 which, for example, can be made of silica glass with a length of 55 mm and a circular cross section with a diameter of 8 mm.

As was already described above referring to the surface 4, the input radiation surface 13 is provided with a structure of microlenses arranged next to one another. In this case, also, the laser radiation is divided into a plurality of partial beams when passing through the input radiation surface 13 and the intensity distribution is homogenized in this way.

Within the beam-guiding rod 14, the laser beam is sent on by total reflection, wherein a further homogenization is achieved. Accordingly, a laser beam whose cross section has a radiation intensity which is uniform into the edge areas is available at the emission surface 15 that is placed on the treatment area 7.

However, it can also be provided that the cross section of the beam-guiding rod 14 tapers in the shape of a truncated cone in the beam direction as is shown by way of example in FIG. 4. Therefore, not only is an improved homogenization achieved with the rod 14, but the cross section of the laser beam is also influenced in that the emission surface 15, like the input radiation surface 13, has a circular cross section, but with a smaller diameter (see FIG. 5a). In other construction variants, it is also possible that the emission surface 15 has a cross-sectional shape as shown in FIGS. 5b to 5d, that is, a hexagonal, square or triangular cross section.

In other constructions of the invention, the input radiation surface 13, as is shown in FIG. 6, is plane (FIG. 6a), concave (FIG. 6b) or convex (FIG. 6c). In this way, through interaction with the structured input radiation surface 13, the intensity distribution as well as the cross-sectional shape can be further influenced in a specific manner.

Figure 8:
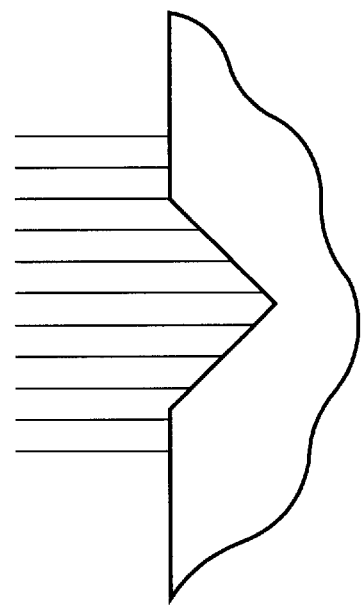
FIG. 8 a cross section through a microstructure.

FIG. 7 is a top view showing a plurality of construction variants of the input radiation surface 13. Various structures are shown in a substantially enlarged view and not in scale. FIG. 7a shows, by way of example, the arrangement of a plurality of lens-like depressions which are randomly distributed over the entire input radiation surface 13. In FIG. 7b, the structure comprises centrically arranged grooves of different diameters, each having a wedge-shaped cross section. A cross section of this kind is shown, for example, in FIG. 8. In FIG. 7c, a helical structure of grooves is provided. FIG. 7d, on the other hand, shows a network of intersecting straight grooves which can also have a cross section according to FIG. 8.

While the foregoing description and drawings represent present invention, it will be obvious to those skilled in the art that various changes may be made therein without departing from the true spirit and scope of the present invention.

What is claimed is:

1. A medical handpiece which is connected with a laser radiation source via a beam guidance device and by which a laser beam is directed to a treatment area, wherein the handpiece is freely moveable relative to the laser beam source, comprising:

at least one optical element with a surface which is structured in the micrometer range and which is accordingly micro-optically active being provided inside the handpiece Following an exit face of the beam guidance device;

wherein the surface has a diffractively acting structure whose width roughly corresponds to the wavelength of the laser beam utilized for treatment and the diffractively acting structure is constructed with a varying height profile with stripe-shaped, cross-shaped funnel-shaped or otherwise shaped raised portions, and the diffractively acting structure is constructed with a varying index of refraction varying within the width of the difractively acting structure; and the difractively acting structure is constructed in the form of a varied absorption coefficient varying within the width of the diffractively acting structure.

2. The medical handpiece according to claim 1, wherein the surface has a refractively acting structure in the form of an array of spherical, aspherical, cylindrical or elliptic, hexagonally or orthogonally arranged, concave or convex lenses, wherein the extension of an individual lens vertical to the beam direction is 10 $\mu$m to 1000 $\mu$m.

3. The medical handpiece according to claim 1, wherein a device for beam focusing is arranged in front of or behind the optical element.

4. The medical handpiece according to claim 3, wherein the device for beam focusing is a collective lens.

5. The medical handpiece according to claim 1, wherein zoom optics are arranged following the optical element.

6. The medical handpiece according to claim 1, wherein the optical element is constructed as a beam-guiding rod in which the beam is relayed by total reflection and which has an input radiation surface and an emission surface for the laser beam, wherein input radiation surface is structured so as to be refractively active.

7. The medical handpiece according to claim 6, wherein the emission surface has a circular cross section.

8. The medical handpiece according to claim 6, wherein the emission surface has a polygonal cross section.

9. The medical handpiece according to claim 8, wherein the emission surface has a square cross section.

10. The medical handpiece according to claim 8, wherein the emission surface has a hexagonal cross section.

11. The medical handpiece according to claim 1, wherein the structured surface is curved.

12. The medical handpiece of claim 11, wherein the curved surface structure is concave.

13. The medical handpiece according to claim 11, wherein the curved structure is convex.

14. The medical handpiece according to claim 1, wherein a ruby laser is provided as laser radiation source.

15. The medical handpiece according to claim 1, wherein a layer of a medium transparent for the laser radiation is provided between the emission surface and the treatment area.

16. The medical handpiece according to claim 15, wherein said layer is an ultrasound gel.

17. The medical handpiece according to claim 15, wherein an ultrasound gel is applied as medium to the treatment area up to a thickness of 1 mm.

18. The medical handpiece according to claim 15, wherein said layer is a gel.

19. A method for cosmetic treatment of skin surfaces using a handpiece according to claim 1, wherein a medium is applied to the emission surface or to the treatment area before the treatment is started, by which medium the reflection of the laser beam from the skin is reduced and the efficiency of the introduction of energy onto the skin is increased.

* * * * *